United States Patent
Douce et al.

(10) Patent No.: US 9,651,527 B2
(45) Date of Patent: May 16, 2017

(54) RING SHAPED COUNTER ELECTRODE TO IMPROVE BEAM STABILITY AND COMPOUND SENSITIVITY ON A CERAMIC TILE TYPE MICROFLUIDIC DEVICE

(71) Applicant: Micromass UK Limited, Wilmslow (GB)

(72) Inventors: David S. Douce, Congleton (GB); John Chipperfield, Manchester (GB); Stevan Bajic, Sale (GB); James Murphy, Franklin, MA (US); David Gordon, Manchester (GB)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 14/956,781

(22) Filed: Dec. 2, 2015

(65) Prior Publication Data
US 2016/0153944 A1 Jun. 2, 2016

Related U.S. Application Data

(60) Provisional application No. 62/086,446, filed on Dec. 2, 2014.

(30) Foreign Application Priority Data

Dec. 15, 2014 (EP) .................................... 14197854

(51) Int. Cl.
*G01N 30/24* (2006.01)
*G01N 30/60* (2006.01)
(Continued)

(52) U.S. Cl.
CPC ........ *G01N 30/7266* (2013.01); *H01J 49/165* (2013.01)

(58) Field of Classification Search
CPC ........... G01N 30/6095; G01N 30/7266; G01N 30/00; G01N 30/06; G01N 30/20; G01N 30/32; G01N 30/463; G01N 30/466; G01N 30/482; G01N 30/6034; G01N 30/606; G01N 30/16; G01N 30/34; G01N 27/44791; G01N 27/447; G01N 27/44743; G01N 27/44782; G01N 1/4005; G01N 21/6428; G01N 21/6445; G01N 21/6458;
(Continued)

(56) References Cited

U.S. PATENT DOCUMENTS 6,464,866 B2 10/2002 Moon et al.
6,605,472 B1 * 8/2003 Skinner ............ B01L 3/502707
204/601
(Continued)

FOREIGN PATENT DOCUMENTS

WO 00/52455 9/2000

*Primary Examiner* — David A Vanore
(74) *Attorney, Agent, or Firm* — Diederiks & Whitelaw, PLC (57) ABSTRACT

An interface for a mass spectrometer is disclosed comprising a microfluidic substrate, tile or cartridge 1 comprising a liquid chromatography separation column and an electrospray emitter 2. A counter electrode 4 is arranged downstream of a tip of the electrospray emitter 2 and is arranged and adapted to direct ions towards an atmospheric pressure interface or ion inlet aperture 5 of a mass spectrometer.

15 Claims, 5 Drawing Sheets

(51) Int. Cl.
*G01N 30/72* (2006.01)
*H01J 49/16* (2006.01)

(58) Field of Classification Search
CPC .. G01N 33/536; G01N 33/542; G01N 33/543; G01N 33/6845; G01N 33/6854; H01J 49/04; H01J 49/165; H01J 49/067; H01J 49/00; H01J 49/0009; H01J 49/045; H01J 27/26; B01L 3/0268; B01L 3/5027; B01L 3/50273
USPC ... 250/281, 288, 282, 423 R, 286, 424, 428, 250/283, 285, 287, 425, 493.1, 503.1, 250/505.1; 210/198.2, 656, 199, 200, 210/253; 422/70, 400, 129, 503, 68.1; 436/180, 161, 174, 178
See application file for complete search history.

(56) References Cited

U.S. PATENT DOCUMENTS

| | | | |
|---|---|---|---|
| 6,822,231 B2 | 11/2004 | Schultz et al. | |
| 6,858,842 B2 | 2/2005 | Moon et al. | |
| 6,967,324 B2* | 11/2005 | Goodley | H01J 49/0018 250/281 |
| 7,067,804 B2* | 6/2006 | Chen | H01J 49/165 250/281 |
| 7,204,431 B2 | 4/2007 | Li et al. | |
| 7,391,020 B2* | 6/2008 | Bousse | B05B 5/025 250/281 |
| 7,829,847 B2* | 11/2010 | Chiarot | B01L 3/5027 250/281 |
| 7,960,711 B1* | 6/2011 | Sheehan | H01J 49/045 250/281 |
| 7,976,779 B2* | 7/2011 | Tai | G01N 30/34 204/450 |
| 8,242,441 B2* | 8/2012 | Wouters | H01J 49/167 210/198.2 |
| 9,159,537 B2 | 10/2015 | McGivney et al. | |
| 9,302,225 B2* | 4/2016 | Whitehouse | G01N 30/7266 |
| 9,304,116 B2* | 4/2016 | Murphy | H01J 49/0431 |
| 9,396,916 B2* | 7/2016 | Gerhardt | H01J 49/0009 |
| 9,496,125 B2* | 11/2016 | Bunner | B01L 3/502792 |
| 9,534,216 B2* | 1/2017 | Link | C12N 15/1075 |
| 2002/0063107 A1* | 5/2002 | Moon | B05B 5/00 216/2 |
| 2002/0139751 A1* | 10/2002 | Zhang | B01J 20/3274 210/656 |
| 2002/0197733 A1* | 12/2002 | Bohm | B01D 57/02 436/180 |
| 2003/0015425 A1* | 1/2003 | Bohm | B01D 57/02 204/453 |
| 2004/0124085 A1* | 7/2004 | Tai | B01L 3/0268 204/600 |
| 2006/0022130 A1 | 2/2006 | Bousse et al. | |
| 2006/0193748 A1* | 8/2006 | Tai | G01N 30/34 422/70 |
| 2007/0158192 A1 | 7/2007 | Timperman et al. | |
| 2008/0235948 A1* | 10/2008 | Bousse | B05B 5/025 29/890.09 |
| 2009/0321356 A1* | 12/2009 | Gerhardt | G01N 30/6095 210/656 |
| 2010/0171055 A1* | 7/2010 | Dourdeville | B23K 20/023 251/129.11 |
| 2014/0047907 A1* | 2/2014 | Murphy | H01J 49/0431 73/61.55 |

\* cited by examiner

RING SHAPED COUNTER ELECTRODE TO IMPROVE BEAM STABILITY AND COMPOUND SENSITIVITY ON A CERAMIC TILE TYPE MICROFLUIDIC DEVICE

CROSS-REFERENCE TO RELATED APPLICATION

This application claims priority from and the benefit of U.S. patent application No. 62/086,446 filed on 2 Dec. 2014 and European patent application No. 14197854.4 filed on 15 Dec. 2014. The entire contents of these applications are incorporated herein by reference.

FIELD OF THE INVENTION

The present invention relates to an interface for a mass spectrometer, a mass spectrometer, a method of liquid chromatography and a method of mass spectrometry. Various embodiments relate to a microfluidic substrate, tile or cartridge comprising a liquid chromatography column and integral electrospray emitter.

BACKGROUND

High-performance liquid chromatography ("HPLC") instruments are analytical tools for separating, identifying, and quantifying compounds. Traditional HPLC instruments use analytical columns constructed from stainless-steel tubing. Typically, the tubing has an inner bore diameter of 4.7 mm, and its length ranges from about 5 cm to about 25 cm.

In addition, the analytical column of an HPLC instrument typically has a fritted end fitting attached to a piece of tubing. Particles, typically silica-based, functionalized with a variety of functional moieties, pack the tube.

To achieve optimal separation efficiency, using the completed column, an appropriate flow rate of a mobile phase is important. For a 4.7 mm diameter column packed with 5 μm diameter particles, a desirable flow rate is typically between about 1 mL/min and about 2 mL/min. Minimizing the presence of unswept dead volume in the plumbing of the HPLC instrument is desirable for maintaining separation efficiency.

In an HPLC instrument, an injector is typically used to inject a sample into a flowing mobile phase as a discrete fluidic plug. Dispersion of a plug band as it travels to and/or from the column reduces the ultimate efficiency of the chromatographic system. For example, in a chromatographic system using 4.7 mm column tubing and a mobile phase flowing at 1-2 mL/min, tubing having an outer diameter of 1/16 inch (1.6 mm) and an inner diameter of about 0.010 inch (0.25 mm) is typically used to plumb connections between the various HPLC components (e.g. pump, injector, column, and detector). For these flow rates and tubing dimensions, it is relatively easy to machine port details to tolerances that will ensure minimal band broadening at tubing interfaces.

A desire to reduce mobile-phase solvent consumption, in part, has motivated a trend towards reducing column inner diameter. Thus, several scales of chromatography are now commonly practiced; these are typically defined as shown in Table 1 (where ID is inner diameter.)

TABLE 1

| HPLC scale | Column ID | Typical flow range |
| --- | --- | --- |
| Analytical | 4.7 mm | 1 s mL/min |
| Microbore | 1-2 mm | 100 s μL/min |
| Capillary | 300-500 μm | 10 s μL/min |
| Nano | 50-150 μm | 100 s nL/min |

Microbore HPLC has often been practiced with equipment similar to that used for analytical scale HPLC, with minor modifications. Aside from requiring the exercise of a small degree of additional care in making fittings, microbore HPLC typically requires an operating skill level similar to that of analytical scale HPLC.

In contrast, capillary and nano-scale HPLC require relatively significant changes in HPLC components relative to analytical-scale HPLC. Generation of stable mobile-phase flows of less than about 50 μL/min is relatively difficult using standard open-loop reciprocating HPLC pumps, such as those commonly found in analytical and microbore HPLC systems.

For capillary-scale chromatography, stainless-steel tubing is usable for component interconnections; however, the inner diameter must typically be less than 0.005 inch (less than about 125 μm). Care is generally required in the manufacture of fitting terminations to avoid creation of even minute amounts of dead volume.

For nano-scale chromatography, tubing having inner diameters of about 25-50 μm is typically required to interconnect components of an instrument (e.g. to connect a pump to a separation column). Because stainless-steel tubing is typically unavailable in these dimensions, polyimide-coated fused-silica tubing is typically used. Although fused-silica tubing has excellent dimensional tolerances and very clean, non-reactive interior walls, it is fragile and can be difficult to work with. In addition, interconnection ports should be machined to exacting tolerances to prevent even nanoliters of unswept dead volume.

While the primary motivation to replace analytical-scale HPLC with microbore-scale HPLC may be the desire for reduced solvent consumption, moving to capillary-scale and nano-scale chromatography can support improved detection sensitivity for mass spectrometers, in addition to further reducing solvent consumption, when, for example, flows of less than about 10 μL/min are used. Moreover, capillary-scale or nano-scale systems are often the only options for the sensitive detection typically required for applications involving small amounts of available sample (e.g. neonatal blood screening).

Despite the advantages of capillary-scale and nano-scale chromatography, HPLC users tend to employ microbore-scale and analytical-scale chromatography systems. As described above, these systems typically provide good reliability and relative ease-of-use. In contrast, maintenance of good chromatographic efficiency while operating a capillary-scale or nano-scale chromatographic system requires significant care when plumbing the system (e.g., using tubing to connect pump, injector, column, and detector).

In practice, an operator switching from an analytical or microbore-scale system to a capillary or nano-scale system at times finds that better separation efficiency was achieved with the higher-flow rate (i.e. the analytical or microbore-scale) system. This typically occurs due to insufficiency in the operator's knowledge or experience required to achieve low band-spreading tubing interconnections. Moreover, use of smaller inner-diameter tubing at times can lead to frequent plugging of tubing.

Due the relative difficulty typically encountered with capillary-scale HPLC systems and, even more so, with nano-scale HPLC systems, such systems have primarily been used only when necessary, such as for small sample sizes, and when a relatively skilled operator is available. Thus, analytical laboratories tend to possess more analytical-scale and microbore-scale systems than capillary-scale and nano-scale systems, and do not realize the full benefits available from capillary-scale and nano-scale HPLC.

Separation techniques, such as HPLC, are often utilized in combination with one or more additional analysis techniques, to provide multidimensional information about a sample. For example, mass spectrometry ("MS") can provide molecular weight and structural information. One problem in combining disparate techniques is provision of sample interfaces.

For example, the combination of LC and MS typically requires transport and ionization of a sample eluent produced by LC, for analysis by MS. Soft ionization techniques, such as field desorption, thermospray and electrospray, are beneficial for production of intact molecular ions that originate from high molecular weight molecules such as proteins and peptides. The precise biological application will often determine a preferred soft-ionization technique.

High-performance liquid chromatography ("HPLC") instruments are known comprising an installation chamber for receiving a microfluidic cartridge having an electrospray emitter. The microfluidic cartridge houses a substantially rigid ceramic-based multilayer microfluidic substrate (also referred to herein as a "ceramic tile"). Further details of the known ceramic tile arrangement are disclosed in, for example, US 2009/0321356 (Waters Corporation) which is incorporated herein by reference.

For protein samples, the ceramic may comprise a High-Temperature Co-fired Ceramic ("HTCC") which provides suitably low levels of loss of sample due to attachment of sample to walls of conduits in the substrate. Formed in the layers of the substrate is a channel that operates as a separation column.

Apertures in the side of the substrate provide openings into the channel through which fluid may be introduced into the separation column formed within the ceramic tile. Fluid passes through the apertures under high pressure and flows toward the electrospray emitter coupled at the egress end of the channel. Holes in the side of the microfluidic cartridge provide fluidic inlet ports for delivering high pressure fluid to the substrate.

A problem with the known ceramic-based microfluidic substrate is that it requires a relatively high capillary voltage to be applied to the electrospray emitter for optimum performance. A high capillary voltage increases the likelihood of electrical discharge which may damage and decrease the lifetime of hardware components such as the emitter tip.

WO 00/52455 (Schultz) discloses a droplet/electrospray device and a nano-scale liquid chromatography-electrospray system.

The electrospray device disclosed in WO 00/52455 (Schultz) is microchip-based having a nozzle etched from a surface of a monolithic silicon substrate. FIG. 3E, for example, shows the electrospray device in use wherein an extracting electrode may be held at a voltage Vextract. In an arrangement, the ion-sampling orifice of an API mass spectrometer may function as the extracting electrode. These conventional electrospray devices do not include an integrated liquid chromatography device and do not provide an interface for combined LC and MS analysis.

In this conventional arrangement the extracting electrode is not a distinct counter electrode arranged downstream of the spray emitted from the capillary tip and upstream of an atmospheric pressure interface of a mass spectrometer. In the conventional arrangement, therefore, the ion-sampling orifice of the mass spectrometer functions as an electrode. The conventional arrangement suffers from the problem of a dispersive electric field at the tip of the electrospray emitter and does not help to reduce capillary voltages. Furthermore, the various components of the ion-sampling orifice of the mass spectrometer function as an electrode which is remote from the tip. As a result, a dispersive field is formed which results in ion beam spreading. Furthermore, the strongly divergent electric field lines may terminate on the inner surface of the ion-sampling orifice cone and ions entering the orifice can thus be lost to the inner walls of the cone. As a result, the ion beam has reduced penetration into the first vacuum region of a mass spectrometer and the sensitivity of the mass spectrometer is reduced.

It is apparent, therefore, that the arrangement disclosed in WO 00/52455 (Schultz) is problematic.

FIG. 6C of WO 00/52455 (Schultz) discloses an arrangement wherein a nano-scale liquid chromatography device may be integrated with an electrospray device. The device includes electrodes that are formed on a recessed annular region and on an ejection surface. In this arrangement the various components of the ion-sampling orifice of the mass spectrometer function as an electrode and as a result the electric field at the tip of the electrospray emitter is dispersive which is problematic.

US 2005/0092855 (Li) discloses an arrangement wherein an electrospray apparatus is provided with an auxiliary electrode.

WO 01/91158 (Chen) discloses an arrangement wherein an ion lens is used to focus ions to the inlet of a downstream mass spectrometer.

US 2009/045333 (Chiarot) discloses an electrospray emitter having an electrode and method of using the same.

US 2004/036019 (Goodley) discloses a source of ions for an analyser which includes an electrode.

It is desired to provide an improved interface for a mass spectrometer.

SUMMARY

According to an aspect there is provided an interface for a mass spectrometer comprising:

a microfluidic substrate, tile or cartridge comprising a liquid chromatography separation column and an electrospray emitter; and a counter electrode arranged downstream from a tip of the electrospray emitter and arranged and adapted to direct ions towards an atmospheric pressure interface or ion inlet aperture of a mass spectrometer.

The approach according to various embodiments is particularly advantageous in that a counter electrode is arranged a short distance downstream of a tip of the electrospray emitter which results in a downstream electric field which has a less dispersive impact upon the ions and which helps to prevent the ion beam from spreading. As a result, the ion beam has an enhanced penetration into a first vacuum region of a downstream mass spectrometer which is particularly advantageous. Furthermore, the embodiments are particularly advantageous when compared to flush and/or upstream electrode arrangements since the counter electrode arranged downstream of the tip of the electrospray emitter results in a less dispersive electric field at the tip of the electrospray emitter. The counter electrode advantageously serves to increase sensitivity whilst simultaneously allowing a reduced capillary voltage to be utilised.

FIGS. 2B to D and 3E to G of WO 00/52455 (Schultz) disclose an electrospray device and an extracting electrode. FIGS. 2B to D and 3E to G of WO 00/52455 (Schultz) do not disclose a microfluidic substrate, tile or cartridge comprising a liquid chromatography separation column and an electrospray emitter. Furthermore, the extracting electrode arrangement disclosed in WO 00/52455 (Schultz) is not a counter electrode which is arranged and adapted to direct ions towards an atmospheric pressure interface or ion inlet aperture of a mass spectrometer. In contrast, the extracting electrode arrangement in WO 00/52455 (Schultz) refers to an ion-sampling orifice of an API mass spectrometer. Such arrangements suffer from a dispersive electric field at the tip of the electrospray emitter and do not allow a reduced capillary voltage to be utilised.

FIG. 6C of WO 00/52455 (Schultz) discloses a different arrangement wherein a microchip-based liquid chromatography device is integrated with an electrospray device without an extracting electrode. WO 00/52455 (Schultz) does not disclose providing a counter electrode arranged downstream from a tip of the electrospray emitter of the device. The electrode arrangement disclosed in WO 00/52455 (Schultz) is not arranged downstream from a tip of the electrospray emitter. In contrast, the electrodes disclosed in FIG. 6C of WO 00/52455 (Schultz) are arranged flush with and upstream of an ejection surface. Such an arrangement of electrodes results in an overall arrangement which causes there to be a dispersive electric field at the tip of the electrospray emitter. As will be appreciated from the above discussion, such an arrangement is therefore problematic.

WO 01/91158 (Chen) does not disclose providing a microfluidic substrate, tile or cartridge comprising a liquid chromatography separation column and an electrospray emitter wherein a counter electrode is arranged downstream from a tip of the electrospray emitter. The ion lens disclosed in WO 01/91158 (Chen) is not a counter electrode arranged downstream of a tip of the electrospray emitter.

US 2005/0092855 (Li) also does not disclose providing a microfluidic substrate, tile or cartridge comprising a liquid chromatography separation column and an electrospray emitter.

US 2009/045333 (Chiarot) also does not disclose providing a microfluidic substrate, tile or cartridge comprising a liquid chromatography separation column and an electrospray emitter. The electrode disclosed in US 2009/045333 (Chiarot) is not arranged and adapted to direct ions towards an atmospheric pressure interface or ion inlet aperture of a mass spectrometer. In contrast, the electrode disclosed in US 2009/045333 (Chiarot) forms an inlet to a mass spectrometer.

US 2004/036019 (Goodley) also does not disclose providing a microfluidic substrate, tile or cartridge comprising a liquid chromatography separation column and an electrospray emitter.

According to various embodiments a ring-shaped counter electrode is positioned in close proximity to or adjacent to or ideally downstream from the spray emitted from the capillary tip of the microfluidic substrate, tile or cartridge. According to various embodiments the counter electrode may be arranged at a distance 1-2 mm, 2-3 mm, 3-4 mm, 4-5 mm, 5-6 mm, 6-7 mm, 7-8 mm, 8-9 mm or 9-10 mm downstream of the tip of the electrospray emitter. The counter electrode advantageously serves to increase sensitivity whilst simultaneously allowing a reduced capillary voltage to be utilised.

The observed benefit is most notable in negative ionization mode but is also observed in positive ionization mode. A voltage bias may be applied to the counter electrode in order to further improve the sensitivity.

The addition of the counter electrode according to embodiments provides a pseudo ground (between the electrospray capillary and the mass spectrometer inlet aperture) which facilitates field enhancement at the capillary tip for lower applied voltages and reduces the spray divergence in the vicinity of the inlet aperture thereby increasing the sampling efficiency.

In the absence of a counter electrode ring, the effective ground is provided by a number of mechanical components and the field from the sharp tipped electrospray capillary is quite dispersive resulting in the requirement of a relatively high capillary voltage since these components are relatively remote from the tip. The counter electrode provides a close proximity surface which creates a uniform field at the capillary tip and further shapes the field at the inlet aperture of a mass spectrometer. The addition of a potential (of a positive or negative polarity) to the counter electrode can be adjusted to optimize the steering field in front of the inlet aperture of the mass spectrometer.

The present embodiments advantageously improve beam stability in negative ionisation mode whilst also increasing sensitivity of a range of compounds in both positive and negative ionisation modes. At the same time these effects are achieved at reduced capillary voltages which has the additional benefit of extending the lifetime of hardware components such as the tile emitter tip.

The various embodiments are particularly advantageous since the counter electrode arranged downstream of the tip of the electrospray emitter results in a downstream electric field which has a less dispersive impact upon the ions and which helps to prevent the ion beam from spreading. As a result, the ion beam has an enhanced penetration into the first vacuum region of a mass spectrometer which is particularly advantageous. Furthermore, the embodiments are particularly advantageous when compared to flush and/or upstream electrode arrangements since the counter electrode arranged downstream of the tip of the electrospray emitter results in a less dispersive electric field at the tip of the electrospray emitter.

The counter electrode may be arranged at a distance x mm downstream from the tip of the electrospray emitter, wherein x is ≤10 mm, ≤9 mm, ≤8 mm, ≤7 mm, ≤6 mm, ≤5 mm, ≤4 mm, ≤3 mm, ≤2 mm or ≤1 mm.

The counter electrode may be arranged at a distance x mm downstream from the tip of the electrospray emitter, wherein x is >0 mm, ≥0.5 mm, ≥0.6 mm, ≥0.7 mm, ≥0.8 mm, ≥0.9 mm or ≥1 mm.

According to various embodiments the counter electrode may be arranged at a distance 1-2 mm, 2-3 mm, 3-4 mm, 4-5 mm, 5-6 mm, 6-7 mm, 7-8 mm, 8-9 mm or 9-10 mm downstream of the tip of the electrospray emitter.

The various embodiments are particularly advantageous when compared to flush (x=0 mm) and/or upstream (x<0 mm) electrode arrangements since the counter electrode arranged downstream (x>0 mm) of the tip of the electrospray emitter results in a less dispersive electric field at the tip of the electrospray emitter. The counter electrode advantageously serves to increase sensitivity whilst simultaneously allowing a reduced capillary voltage to be utilised.

The interface may further comprise a voltage device arranged and adapted to apply a voltage to the electrospray emitter so as to maintain a potential difference between the electrospray emitter and the counter electrode.

The potential difference between the electrospray emitter and the counter electrode results in the ionisation of droplets emitted from the electrospray emitter.

In a positive ionisation mode of operation the voltage device may be arranged and adapted to maintain a potential difference of $V_1$ between the electrospray emitter and the counter electrode, wherein $V_1$ is selected from the group consisting of: (i) 0-1.0 kV; (ii) 1.0-1.5 kV; (iii) 1.5-2.0 kV; (iv) 2.0-2.5 kV; and (v) 2.5-3.0 kV.

In a positive ionisation mode of operation the voltage device may be arranged and adapted to maintain the counter electrode at a potential selected from the group consisting of: (i) <−200 V; (ii) −200 to −100 V; (iii) −100V to 0V; (iv) 0V; (v) 0-100 V; (vi) 100-200 V; and (vii) >200 V.

In a negative ionisation mode of operation the voltage device may be arranged and adapted to maintain a potential difference of $V_2$ between the electrospray emitter and the counter electrode, wherein $V_2$ is selected from the group consisting of: (i) 0 to −1.0 kV; (ii) −1.0 to −1.5 kV; (iii) −1.5 to −2.0 kV; (iv) −2.0 to −2.5 kV; and (v) −2.5 to −3.0 kV.

In a negative ionisation mode of operation the voltage device may be arranged and adapted to maintain the counter electrode at a potential selected from the group consisting of: (i) <−200 V; (ii) −200 to −100 V; (iii) −100V to 0V; (iv) 0V; (v) 0-100 V; (vi) 100-200 V; and (vii) >200 V.

According to various embodiments in use a liquid sample is passed through the liquid chromatography separation column at a flow rate <250 nL/min, 250-500 nL/min, 500-750 nL/min, 750-1000 nL/min, 1-2 μL/min, 2-3 μL/min, 3-4 μL/min, 4-5 μL/min, 5-6 μL/min, 6-7 μL/min, 7-8 μL/min, 8-9 μL/min, 9-10 μL/min, 10-15 μL/min and/or 15-20 μL/min.

An important advantage of the various embodiments is that the spray divergence is reduced at these flow rates and the capillary emitter voltage is lower due to the proximity of the electrode to the emitter (same field strength at a lower applied voltage). Accordingly, the ion beam towards the ring aperture orifice is significantly stabilised due to geometric uniformity and a reduced likelihood of electrical discharges.

The interface may further comprise a device arranged and adapted to introduce a nebulising flow of gas around the tip of the electrospray emitter.

The interface may be arranged and adapted such that the transport of charged droplets produced at the tip of the electrospray emitter is dominated by gas flow.

A particular advantage of the various embodiments is that at these flow rates, charged droplets may be predominantly produced at the tip of the electrospray emitter which initially follow the nebuliser gas flow lines upstream of the counter electrode, since the drag force exceeds the electrostatic force. Gas phase ions that are produced downstream of the counter electrode can then benefit from the counter electrode-defined electric field. As a result, the ions may be less dispersed and sampling of the ions at the ion inlet orifice of a mass spectrometer may be increased, which is particularly advantageous.

The counter electrode may comprise a ring or annular electrode or an electrode having one or more apertures.

The counter electrode may be arranged so that droplets and/or analyte ions emitted in use from the electrospray emitter pass through one or more apertures in the counter electrode.

The interface may further comprise a voltage supply arranged and adapted to supply a DC voltage to the counter electrode and/or the electrospray emitter.

The interface may further comprise a voltage supply arranged and adapted to supply an AC or RF voltage to the counter electrode and/or the electrospray emitter.

The counter electrode may be arranged and adapted to create a substantially uniform electric field at or in the vicinity of the electrospray emitter.

The counter electrode may be arranged and adapted to be maintained at a higher or lower voltage or potential than the electrospray emitter or at ground (0V).

The microfluidic substrate may comprise a multi-layered planar structure and the liquid chromatography separation column may comprise a channel formed within the multi-layered planar structure.

The microfluidic substrate, tile or cartridge may be formed from a ceramic or is otherwise formed from sintered inorganic particles.

The various embodiments are particularly advantageous in that the counter electrode allows a reduced capillary voltage to be applied, thereby decreasing the likelihood of electrical discharge and extending the lifetime of hardware components such as the emitter tip.

The liquid chromatography separation column may have a width selected from the group consisting of: (i) ≤500 μm; (ii) ≤400 μm; (iii) ≤300 μm; (iv) ≤200 μm; and (v) ≤100 μm.

The interface may further comprise a pump which is arranged and adapted to deliver a liquid comprising a solvent to the microfluidic substrate, tile or cartridge at a pressure ≥1 kpsi, ≥2 kpsi, ≥3 kpsi, ≥4 kpsi, ≥5 kpsi, ≥6 kpsi, ≥7 kpsi, ≥8 kpsi, ≥9 kpsi, ≥10 kpsi, ≥11 kpsi, ≥12 kpsi, ≥13 kpsi, ≥14 kpsi or ≥15 kpsi.

The electrospray emitter may form an integral part of the microfluidic substrate, tile or cartridge.

The microfluidic substrate, tile or cartridge may further comprise at least one of: (i) an integral high pressure fluidic fitting; (ii) an integral voltage connection for a heater; (iii) an integral temperature sensor; and (iv) an integral gas connection for a nebuliser gas.

According to another aspect there is provided a mass spectrometer comprising an interface as described above.

The mass spectrometer may comprise an atmospheric pressure interface comprising an outer gas cone and an inner sampling cone, capillary interface or other gas limiting interface.

The potential difference between the outer gas cone and the counter electrode may be arranged to be 0-50 V, 50-100 V, 100-150 V or 150-200 V.

According to another aspect there is provided a method of liquid chromatography comprising:

passing a liquid through a microfluidic substrate, tile or cartridge comprising a liquid chromatography separation column and electrospray emitter;

ionising an eluent emitted from the liquid chromatography column using the electrospray emitter;

providing a counter electrode downstream from a tip of the electrospray emitter; and directing ions using the counter electrode towards an atmospheric pressure interface or ion inlet aperture of a mass spectrometer.

The method may further comprise locating the counter electrode at a distance x mm downstream from the tip of the electrospray emitter, wherein x is ≤10 mm, ≤9 mm, ≤8 mm, ≤7 mm, ≤6 mm, ≤5 mm, ≤4 mm, ≤3 mm, ≤2 mm or ≤1 mm.

The method may further comprise locating the counter electrode at a distance x mm downstream from the tip of the electrospray emitter, wherein x is >0 mm, ≥0.5 mm, ≥0.6 mm, ≥0.7 mm, ≥0.8 mm, ≥0.9 mm or ≥1 mm.

According to various embodiments the counter electrode may be arranged at a distance 1-2 mm, 2-3 mm, 3-4 mm, 4-5 mm, 5-6 mm, 6-7 mm, 7-8 mm, 8-9 mm or 9-10 mm downstream of the tip of the electrospray emitter.

The method may further comprise applying a voltage to the electrospray emitter so as to maintain a potential difference between the electrospray emitter and the counter electrode.

The potential difference between the electrospray emitter and the counter electrode may result in the ionisation of droplets emitted from the electrospray emitter.

The method may further comprise in a positive ionisation mode of operation maintaining a potential difference of $V_1$ between the electrospray emitter and the counter electrode, wherein $V_1$ is selected from the group consisting of: (i) 0-1.0 kV; (ii) 1.0-1.5 kV; (iii) 1.5-2.0 kV; (iv) 2.0-2.5 kV; and (v) 2.5-3.0 kV.

The method may further comprise in a positive ionisation mode of operation maintaining the counter electrode at a potential selected from the group consisting of: (i) <−200 V; (ii) −200 to −100 V; (iii) −100V to 0V; (iv) 0V; (v) 0-100 V; (vi) 100-200 V; and (vii) >200 V.

The method may further comprise in a negative ionisation mode of operation maintaining a potential difference of $V_2$ between the electrospray emitter and the counter electrode, wherein $V_2$ is selected from the group consisting of: (i) 0 to −1.0 kV; (ii) −1.0 to −1.5 kV; (iii) −1.5 to −2.0 kV; (iv) −2.0 to −2.5 kV; and (v) −2.5 to −3.0 kV.

The method may further comprise in a negative ionisation mode of operation maintaining the counter electrode at a potential selected from the group consisting of: (i) <−200 V; (ii) −200 to −100 V; (iii) −100V to 0V; (iv) 0V; (v) 0-100 V; (vi) 100-200 V; and (vii) >200 V.

The method may further comprise passing a liquid sample through the liquid chromatography separation column at a flow rate <250 nL/min, 250-500 nL/min, 500-750 nL/min, 750-1000 nL/min, 1-2 μL/min, 2-3 μL/min, 3-4 μL/min, 4-5 μL/min, 5-6 μL/min, 6-7 μL/min, 7-8 μL/min, 8-9 μL/min, 9-10 μL/min, 10-15 μL/min and/or 15-20 μL/min.

The method may further comprise introducing a nebulising flow of gas around the tip of the electrospray emitter.

The method may further comprise applying a DC voltage to the counter electrode and/or the electrospray emitter.

The method may further comprise applying an AC or RF voltage to the counter electrode and/or the electrospray emitter.

The method may further comprise using the counter electrode to create a substantially uniform electric field at or in the vicinity of the electrospray emitter.

The method may further comprise maintaining the counter electrode at a higher or lower voltage or potential than the electrospray emitter or at ground (0V).

The method may further comprise delivering a liquid comprising a solvent to the microfluidic substrate, tile or cartridge at a pressure ≥1 kpsi, ≥2 kpsi, ≥3 kpsi, ≥4 kpsi, ≥5 kpsi, ≥6 kpsi, ≥7 kpsi, ≥8 kpsi, ≥9 kpsi, ≥10 kpsi, ≥11 kpsi, ≥12 kpsi, ≥13 kpsi, ≥14 kpsi or ≥15 kpsi.

According to an aspect there is provided an Electrospray ionisation source for a mass spectrometer comprising:
an electrospray emitter;
a counter electrode having one or more apertures arranged downstream of the electrospray emitter; and
a voltage device arranged and adapted to maintain a potential difference between the electrospray emitter and the counter electrode so as to ionise droplets emitted from the electrospray emitter to form analyte ions, wherein the analyte ions pass in use through the one or more apertures towards an atmospheric pressure interface of a mass spectrometer.

The present embodiments are particularly advantageous since the counter electrode arranged downstream of the electrospray emitter results in a downstream electric field which has a less dispersive impact upon the ions and which helps to prevent the ion beam from spreading. As a result, the ion beam has an enhanced penetration into the first vacuum region of a mass spectrometer which is particularly advantageous.

The Electrospray ionisation source may further comprise a device arranged and adapted to pass a liquid sample through the electrospray emitter at a flow rate <250 nL/min, 250-500 nL/min, 500-750 nL/min, 750-1000 nL/min, 1-2 μL/min, 2-3 μL/min, 3-4 μL/min, 4-5 μL/min, 5-6 μL/min, 6-7 μL/min, 7-8 μL/min, 8-9 μL/min, 9-10 μL/min, 10-15 μL/min and/or 15-20 μL/min.

The counter electrode may be arranged at a distance 1-2 mm, 2-3 mm, 3-4 mm, 4-5 mm, 5-6 mm, 6-7 mm, 7-8 mm, 8-9 mm or 9-10 mm downstream of a tip of the electrospray emitter.

A particular advantage of the various embodiments is that the spray divergence is reduced at these flow rates and the capillary emitter voltage is lower due to the proximity of the electrode to the emitter (same field strength at a lower applied voltage). Accordingly, the ion beam towards the ring aperture orifice is significantly stabilised due to geometric uniformity and a reduced likelihood of electrical discharges.

According to another aspect there is provided a method of Electrospray ionisation comprising:
maintaining a potential difference between an electrospray emitter and a counter electrode having one or more apertures arranged downstream of the electrospray emitter so as to ionise droplets emitted from the electrospray emitter to form analyte ions, wherein the analyte ions pass through the one or more apertures towards an atmospheric pressure interface of a mass spectrometer.

The method may further comprise passing a liquid sample through the electrospray emitter at a flow rate <250 nL/min, 250-500 nL/min, 500-750 nL/min, 750-1000 nL/min, 1-2 μL/min, 2-3 μL/min, 3-4 μL/min, 4-5 μL/min, 5-6 μL/min, 6-7 μL/min, 7-8 μL/min, 8-9 μL/min, 9-10 μL/min, 10-15 μL/min and/or 15-20 μL/min.

The method may further comprise arranging a counter electrode to be located at a distance 1-2 mm, 2-3 mm, 3-4 mm, 4-5 mm, 5-6 mm, 6-7 mm, 7-8 mm, 8-9 mm or 9-10 mm downstream of a tip of the electrospray emitter.

According to an aspect there is provided an interface for a mass spectrometer comprising:
a microfluidic substrate, tile or cartridge comprising a liquid chromatography separation column and an electrospray emitter; and
a counter electrode arranged adjacent to the electrospray emitter.

The counter electrode may be arranged downstream from a tip of the electrospray emitter.

The counter electrode may be arranged at a distance x mm downstream from a tip of the electrospray emitter, wherein x is ≤10 mm, ≤9 mm, ≤8 mm, ≤7 mm, ≤6 mm, ≤5 mm, ≤4 mm, ≤3 mm, ≤2 mm or ≤1 mm.

The counter electrode may be arranged and adapted to direct ions towards an atmospheric pressure interface or ion inlet aperture of a mass spectrometer.

According to another aspect of the present invention there is provided a method of liquid chromatography comprising:

passing a liquid through a microfluidic substrate, tile or cartridge comprising a liquid chromatography separation column and electrospray emitter;

ionising an eluent emitted from the liquid chromatography column using the electrospray emitter; and providing a counter electrode adjacent to the electrospray emitter.

The method may further comprise locating the counter electrode at a distance x mm downstream from a tip of the electrospray emitter, wherein x is ≤10 mm, ≤9 mm, ≤8 mm, ≤7 mm, ≤6 mm, ≤5 mm, ≤4 mm, ≤3 mm, ≤2 mm or ≤1 mm.

The method may further comprise directing ions using the counter electrode towards an atmospheric pressure interface or ion inlet aperture of a mass spectrometer.

The spectrometer may comprise an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source.

The spectrometer may comprise one or more continuous or pulsed ion sources.

The spectrometer may comprise one or more ion guides.

The spectrometer may comprise one or more ion mobility separation devices and/or one or more Field Asymmetric Ion Mobility Spectrometer devices.

The spectrometer may comprise one or more ion traps or one or more ion trapping regions.

The spectrometer may comprise one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device.

The spectrometer may comprise a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser.

The spectrometer may comprise one or more energy analysers or electrostatic energy analysers.

The spectrometer may comprise one or more ion detectors.

The spectrometer may comprise one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter.

The spectrometer may comprise a device or ion gate for pulsing ions; and/or a device for converting a substantially continuous ion beam into a pulsed ion beam.

The spectrometer may comprise a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser.

The spectrometer may comprise a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The spectrometer may comprise a device arranged and adapted to supply an AC or RF voltage to the electrodes. The AC or RF voltage optionally has an amplitude selected from the group consisting of: (i) about <50 V peak to peak; (ii) about 50-100 V peak to peak; (iii) about 100-150 V peak to peak; (iv) about 150-200 V peak to peak; (v) about 200-250 V peak to peak; (vi) about 250-300 V peak to peak; (vii) about 300-350 V peak to peak; (viii) about 350-400 V peak to peak; (ix) about 400-450 V peak to peak; (x) about 450-500 V peak to peak; and (xi) >about 500 V peak to peak.

The AC or RF voltage may have a frequency selected from the group consisting of: (i) <about 100 kHz; (ii) about 100-200 kHz; (iii) about 200-300 kHz; (iv) about 300-400 kHz; (v) about 400-500 kHz; (vi) about 0.5-1.0 MHz; (vii) about 1.0-1.5 MHz; (viii) about 1.5-2.0 MHz; (ix) about 2.0-2.5 MHz; (x) about 2.5-3.0 MHz; (xi) about 3.0-3.5 MHz; (xii) about 3.5-4.0 MHz; (xiii) about 4.0-4.5 MHz; (xiv) about 4.5-5.0 MHz; (xv) about 5.0-5.5 MHz; (xvi) about 5.5-6.0 MHz; (xvii) about 6.0-6.5 MHz; (xviii) about 6.5-7.0 MHz; (xix) about 7.0-7.5 MHz; (xx) about 7.5-8.0 MHz; (xxi) about 8.0-8.5 MHz; (xxii) about 8.5-9.0 MHz; (xxiii) about 9.0-9.5 MHz; (xxiv) about 9.5-10.0 MHz; and (xxv) >about 10.0 MHz.

The spectrometer may comprise a chromatography or other separation device upstream of an ion source. The chromatography separation device may comprise a liquid chromatography or gas chromatography device. Alternatively, the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <about 0.0001 mbar; (ii) about 0.0001-0.001 mbar; (iii) about 0.001-0.01 mbar; (iv) about 0.01-0.1 mbar; (v) about 0.1-1 mbar; (vi) about 1-10 mbar; (vii) about 10-100 mbar; (viii) about 100-1000 mbar; and (ix) >about 1000 mbar.

Analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

Optionally, in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) C60 vapour or atoms; and (viii) magnesium vapour or atoms.

The multiply charged analyte cations or positively charged ions may comprise peptides, polypeptides, proteins or biomolecules.

Optionally, in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

The process of Electron Transfer Dissociation fragmentation may comprise interacting analyte ions with reagent ions, wherein the reagent ions comprise dicyanobenzene, 4-nitrotoluene or azulene.

A chromatography detector may be provided, wherein the chromatography detector comprises either:

a destructive chromatography detector optionally selected from the group consisting of (i) a Flame Ionization Detector (FID); (ii) an aerosol-based detector or Nano Quantity Analyte Detector (NQAD); (iii) a Flame Photometric Detector (FPD); (iv) an Atomic-Emission Detector (AED); (v) a Nitrogen Phosphorus Detector (NPD); and (vi) an Evaporative Light Scattering Detector (ELSD); or a non-destructive chromatography detector optionally selected from the group consisting of: (i) a fixed or variable wavelength UV detector; (ii) a Thermal Conductivity Detector (TCD); (iii) a fluorescence detector; (iv) an Electron Capture Detector (ECD); (v) a conductivity monitor; (vi) a Photoionization Detector (PID); (vii) a Refractive Index Detector (RID); (viii) a radio flow detector; and (ix) a chiral detector.

The spectrometer may be operated in various modes of operation including a mass spectrometry ("MS") mode of operation; a tandem mass spectrometry ("MS/MS") mode of operation; a mode of operation in which parent or precursor ions are alternatively fragmented or reacted so as to produce fragment or product ions, and not fragmented or reacted or fragmented or reacted to a lesser degree; a Multiple Reaction Monitoring ("MRM") mode of operation; a Data Dependent Analysis ("DDA") mode of operation; a Data Independent Analysis ("DIA") mode of operation a Quantification mode of operation or an Ion Mobility Spectrometry ("IMS") mode of operation.

BRIEF DESCRIPTION OF THE DRAWINGS

Various embodiments will now be described, by way of example only, and with reference to the accompanying drawings in which.

DETAILED DESCRIPTION

A conventional microfluidic tile will first be described in more detail with reference to FIG. 1.

A known microfluidic ceramic tile (for flow rates of less than 20 μl/min) uses electrospray ionization for the quantitative determination of compounds in both positive and negative ionization mode. The tile is particularly prone to electrical discharge in negative ionisation mode. These effects are most pronounced at highly aqueous solvent compositions. It has been observed that these detrimental properties can be alleviated to some extent by the addition of a make-up flow of organic solvent thereby increasing the organic content of the liquid stream that reaches the capillary tip.

Figure 1:
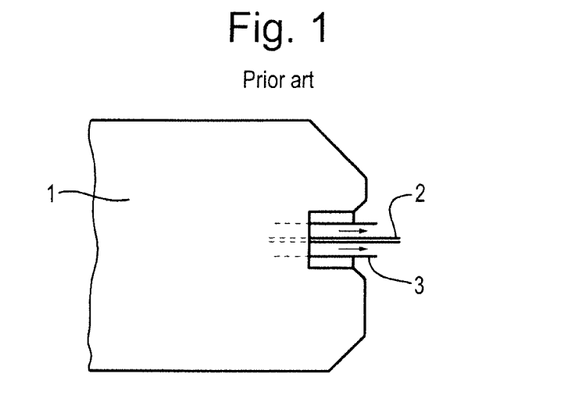
FIG. 1 shows a known microfluidic tile.

FIG. 1 shows in cross-section a known microfluidic tile 1 in which eluent flow exits the tile through a stainless steel sharpened tip capillary 2 (approximately id. 40 μm) at flow rates less than 20 μL/min. Nebulisation of the liquid can be assisted by a flow of gas which is introduced between the capillary 2 and a surrounding collar 3.

In contrast to the known arrangements the present embodiments relate to an interface for a mass spectrometer comprising a microfluidic substrate, tile or cartridge comprising a liquid chromatography separation column and an electrospray emitter wherein a counter electrode is arranged downstream from a tip of the electrospray emitter. The counter electrode is arranged and adapted to direct ions towards an atmospheric pressure interface or ion inlet aperture of a mass spectrometer.

In particular, the counter electrode may be arranged at a distance 1-2 mm, 2-3 mm, 3-4 mm, 4-5 mm, 5-6 mm, 6-7 mm, 7-8 mm, 8-9 mm or 9-10 mm downstream of the tip of the electrospray emitter.

The approach according to various embodiments is particularly advantageous in that a counter electrode is arranged a short distance downstream of a tip of the electrospray emitter which results in a downstream electric field which has a less dispersive impact upon the ions and which helps to prevent the ion beam from spreading. As a result, the ion beam has an enhanced penetration into a first vacuum region of a downstream mass spectrometer which is particularly advantageous. Furthermore, the embodiments are particularly advantageous when compared to flush and/or upstream electrode arrangements since the counter electrode arranged downstream of the tip of the electrospray emitter results in a less dispersive electric field at the tip of the electrospray emitter. The counter electrode advantageously serves to increase sensitivity whilst simultaneously allowing a reduced capillary voltage to be utilised.

Various embodiments will now be described in more detail with reference to FIG. 2.

Figure 2:
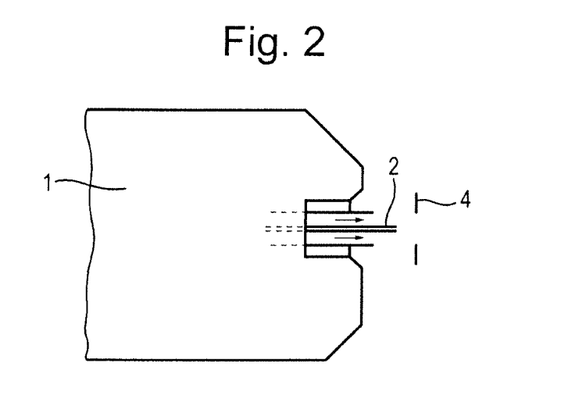
FIG. 2 shows a microfluidic tile according to an embodiment incorporating a counter electrode which is disposed in close proximity to and downstream of the electrospray capillary tip.

The various embodiments relate to a modification to the known existing tile wherein the modification is shown in FIG. 2. In particular, the various embodiments relate to the inclusion of a flat ring-shaped electrode 4 positioned in front of and downstream of the capillary tip 2. The electrode 4 may be arranged at a distance 1-2 mm, 2-3 mm, 3-4 mm, 4-5 mm, 5-6 mm, 6-7 mm, 7-8 mm, 8-9 mm or 9-10 mm downstream of the tip of the electrospray emitter. The electrode 4 acts as a counter electrode to the potential applied at the capillary tip 2. The electrode 4 is particularly advantageous in that the resulting electrical field emanating from the emitter tip is uniform and well-defined. This is in contrast to the conventional configuration where the field generated at the emitter tip 2 is directed in a dispersed manner toward either the sample cone or other source components of a mass spectrometer which are relatively distant from the capillary tip 2.

The ring counter electrode 4 advantageously results in a more stable and high-intensity field that can achieve electrostatic dispersion at significantly reduced capillary voltages.

Figure 3:
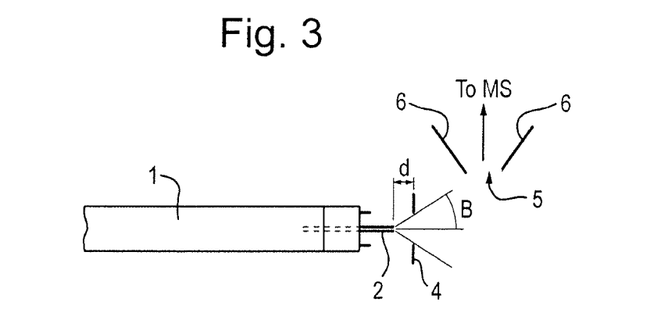
FIG. 3 shows an advantageous orientation of the microfluidic tile and counter electrode relative to an ion inlet orifice of a mass spectrometer.

FIG. 3 shows a plan view of the tile/emitter 1,2 and ring electrode 4 embodiment wherein d is the distance between the capillary tip 2 and the counter electrode 4.

For a point-plane geometry, the electric field E at the capillary tip 2 for a given applied voltage V, point radius r and gap distance d is given by:

$$E = 2V/r \ln(1+4d/r) \qquad (1)$$

For typical electrospray geometries, r<<d and hence the electric field E is given by:

$$E = 2V/r \ln(4d/r) \qquad (2)$$

For a sharpened capillary profile the point radius r will be approximately equal to half the internal diameter of the capillary bore i.e. r=20 μm.

Figure 4:
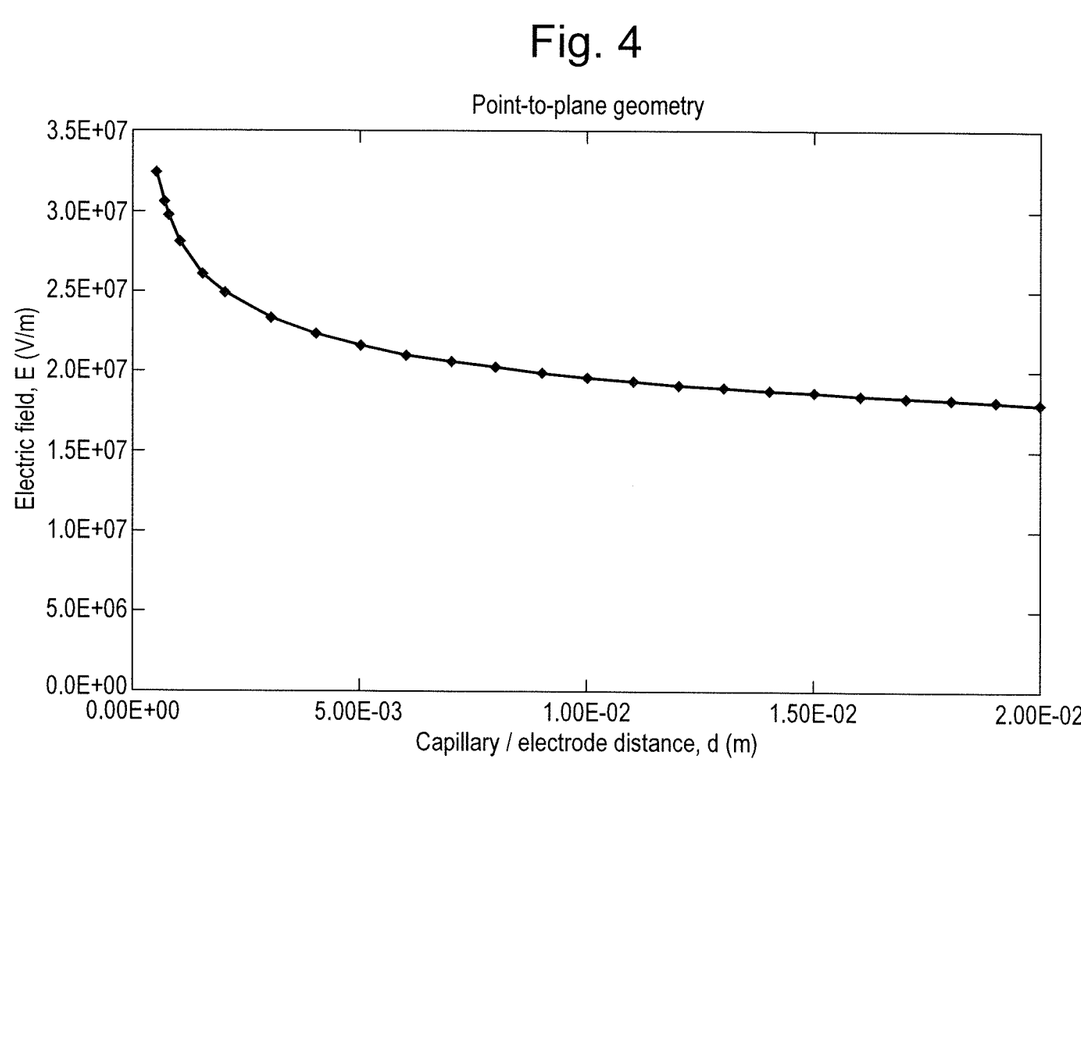
FIG. 4 shows the electric field at the tip of a capillary electrode as a function of the spacing between the tip of the capillary electrode and the counter electrode according to an embodiment.

FIG. 4 shows the dependence of the electric field E at the capillary tip 2 for increasing capillary/electrode distances for the present geometry and an applied capillary voltage of 1.5 kV. As is apparent from FIG. 4, for gap distances >10 mm such as encountered in a conventional arrangement (FIG. 1), the electric field E is very weakly dependent on d.

For gap distances of d<10 mm, the electric field E becomes more dependent on d until a point is reached at approximately d≤5 mm whereupon the dependence increases dramatically.

According to an embodiment a short capillary/electrode distance (e.g. d<5 mm) is maintained in order to significantly increase the electric field strength at the capillary tip 2 for a given applied voltage.

In addition to enhancing the electric field strength at the emitter tip 2, the use of a counter electrode ring 4 results in other benefits with respect to the shape of the electric field between the ring electrode 4 and the ion inlet orifice 5 of a mass spectrometer as shown in FIG. 3.

It is known that a high electric field at the ion inlet orifice 5 is undesirable since this creates strongly divergent electric field lines on the inside of the orifice cone which terminate on the inner surface of the cone. Ions entering the orifice can thus be lost to the inner walls 6 of the cone. Advantageously, these loses are reduced for a reduced-field or field-free region directly upstream of the ion inlet orifice 5 as a result from the use of a pseudo-ground ring electrode 4 according to various embodiments. According to various embodiments the transport of ions is dominated by the gas flow created between the atmospheric pressure source and the vacuum on the downstream side of the inlet orifice.

The use of a lower capillary voltage with a ring electrode 4 according to an embodiment reduces the likelihood of reaching the electrical discharge threshold when at high aqueous conditions. Unwanted discharges result in excessive space charge within the spray plume which results in increased spray divergence and hence reduced sensitivity.

Furthermore, with reference to the plan view shown in FIG. 3, the generation of an electrospray plume via a ring electrode-defined electric field results in a reduced angle of dispersion B thereby resulting in an increased sampling of the ions at the sample cone 5 or outer gas cone of a mass spectrometer.

According to this embodiment the interface for a mass spectrometer comprises a microfluidic substrate, tile or cartridge 1 which comprises a liquid chromatography separation column and an electrospray emitter 2. The interface further comprises a counter electrode 4 which is arranged downstream from the tip of the electrospray emitter 2, which is arranged and adapted to direct ions towards an atmospheric pressure interface or ion inlet aperture 5 of a mass spectrometer.

According to various embodiments the electrospray emitter is operated at capillary-scale and a nebulising flow of gas is introduced between the capillary 2 and the surrounding collar 3. Under these conditions, charged droplets are predominantly produced at the capillary tip 2 which initially follow the nebuliser gas flow lines since the drag force exceeds the electrostatic force. Gas phase ions that are produced downstream of the counter electrode 4 can then benefit from the counter electrode-defined electric field. For example, in positive ionisation mode with a positive capillary voltage, gas phase ions that are produced downstream of the counter electrode 4 particularly benefit from a positive potential applied to the counter electrode 4. As a result, the dispersive nature of the electric field is reduced and sampling of the ions at the ion inlet orifice 5 of a mass spectrometer is increased.

Moreover, the various embodiments are particularly advantageous when compared to nanospray devices. Under the same conditions at nano-scale, a counter electrode 4 positioned downstream of the capillary tip 2 will behave as a collector and will therefore reduce the sampling of the ions at the ion inlet orifice 5. This is due to the fact that gas phase ions are predominantly created at the capillary tip for nanospray flows and these ions will initially follow the electrostatic field lines rather than the nebuliser gas flow lines.

According to these embodiments the interface for a mass spectrometer comprises a microfluidic substrate, tile or cartridge 1 which comprises a liquid chromatography separation column and an electrospray emitter 2. The interface further comprises a counter electrode 4 arranged downstream from the tip of the electrospray emitter 2, which is arranged and adapted to direct ions towards an atmospheric pressure interface or ion inlet aperture 5 of a mass spectrometer. In use a liquid sample is passed through the liquid chromatography separation column at a flow rate <250 nL/min, 250-500 nL/min, 500-750 nL/min, 750-1000 nL/min, 1-2 μL/min, 2-3 μL/min, 3-4 μL/min, 4-5 μL/min, 5-6 μL/min, 6-7 μL/min, 7-8 μL/min, 8-9 μL/min, 9-10 μL/min, 10-15 μL/min and/or 15-20 μL/min. The interface further comprises a device arranged and adapted to introduce a nebulising flow of gas around the tip of the electrospray emitter 3. The interface is arranged and adapted such that the transport of charged droplets produced at the tip of the electrospray emitter is dominated by gas flow.

Infusion experiments were conducted on an orthogonal acceleration Time of Flight mass spectrometer fitted with a microfluidic tile device. Data was obtained using a six component sample, prepared in 50% aqueous acetonitrile, infused through a microfluidic infusion tile at 3 μL/min and at a tile temperature of 40° C. The response of four of these components was monitored in positive ionisation mode and two in negative ionisation mode.

The capillary voltages used without a ring electrode 4 in position were +3.0 kV and −2.2 kV for positive and negative ion modes respectively. With the ring electrode 4 in position the capillary voltages used were in the range of 2.0 to 2.5 kV and −1.2 to −1.5 kV for positive and negative ion modes respectively. A particularly advantageous aspect is that a lower capillary voltage (approx. 1 kV lower) may be utilised which significantly reduces the risk of electrical discharge especially at high aqueous concentrations. Unwanted discharges can result in excessive space charge within the spray plume which results in increased spray divergence and hence a reduction in sensitivity.

Accordingly, the counter electrode 4 and reduced capillary voltage is particularly advantageous.

A 0.5 mm thick circular counter electrode 4 was used with an internal aperture of 3.25 mm and an outer diameter of 8.0 mm. The counter electrode 4 was positioned 1.5 mm from the end of the capillary tip 2. Initially, the ring electrode 4 was grounded and compared to the response achieved without a ring electrode 4 in place. Following this a potential of up to +/−200V was applied to the ring electrode 4 which affected the signal intensity that was achieved.

Figure 5:
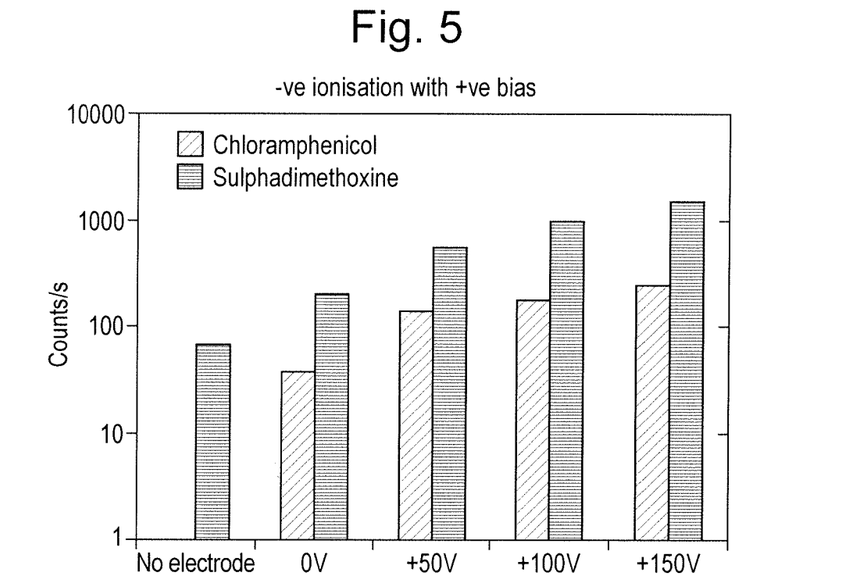
FIG. 5 shows the counts per second obtained in negative ionisation mode for chloramphenicol and sulphadimethoxine in the absence of a counter electrode and with a counter electrode maintained at a bias voltage of 0V, 50V, 100V and 150V.
Figure 6:
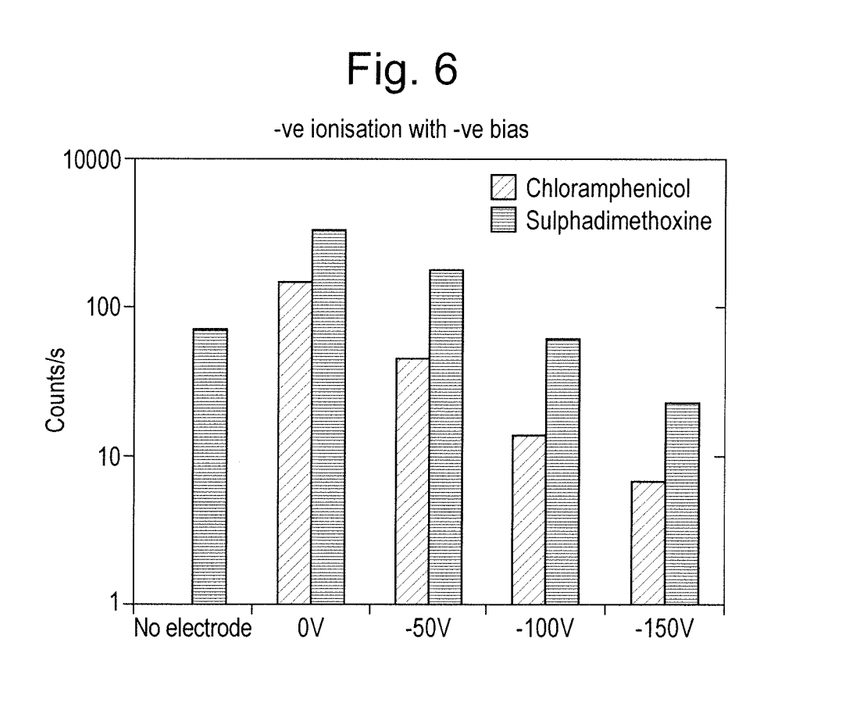
FIG. 6 shows the counts per second obtained in negative ionisation mode for chloramphenicol and sulphadimethoxine in the absence of a counter electrode and with a counter electrode maintained at a bias voltage of 0V, −50V, −100V and −150V.

FIGS. 5 and 6 show the counts per second obtained in negative ionisation mode for chloramphenicol and sulphadimethoxine. FIGS. 5 and 6 show that without a ring electrode 4 no signal was observed for chloramphenicol under these experimental conditions.

Advantageously, the inclusion of the ring electrode 4 but maintained at ground (0V) facilitates a significant signal for chloramphenicol.

The signal for sulphadimethoxine, whilst present without a ring electrode 4, was also enhanced by the presence of the ring electrode 4 even if the ring electrode 4 were maintained at 0V.

FIG. 5 shows that the application of a positive voltage to the ring electrode 4 in negative ionisation mode results in a further enhancement of the signal of chloramphenicol and sulphadimethoxine.

Conversely, FIG. 6 shows that a progressively increasing negative electrode voltage in negative ionisation mode results in a reduction of the signal of both species.

Figure 7A:
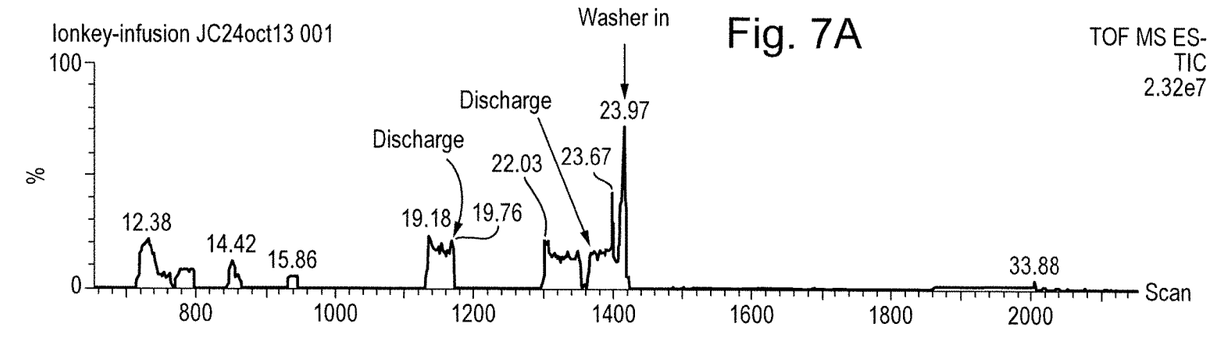
FIG. 7A shows the total ion count of an infusion experiment wherein a solution of chloramphenicol was fed into a microfluidic tile and the mass spectrometer was operated in negative ionisation mode, wherein during the first half of the experiment no ring counter electrode was provided and wherein during the second half of the experiment a ring counter electrode was provided in accordance with an embodiment
Figure 7B:
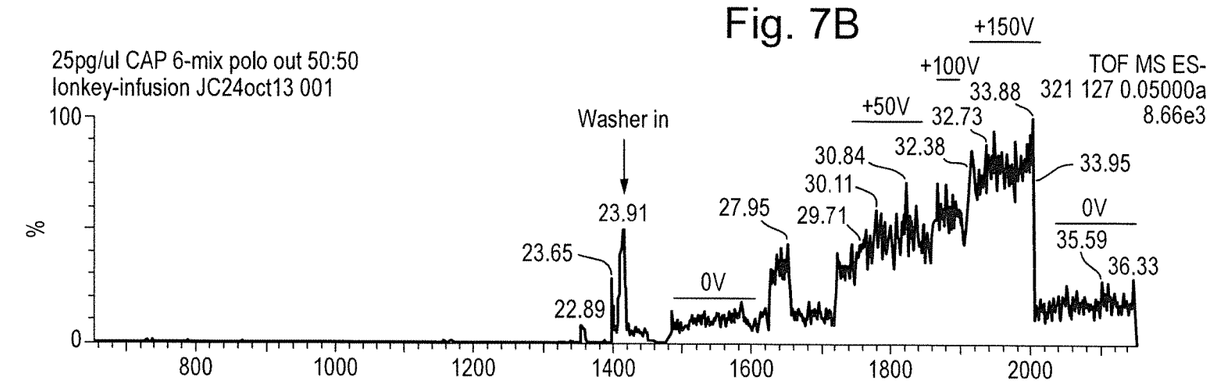
FIG. 7B shows a corresponding extracted ion count of the infusion experiment.

FIG. 7A shows the total ion current ("TIC") and FIG. 7B shows the extracted ion current ("EIC" @ 321.127 m/z) of an infusion experiment wherein a solution of chloramphenicol in 50:50 acetonitrile/water was fed into a microfluidic tile 1 via the onboard fluidics and pump situated within the mass spectrometer. During this experiment the mass spectrometer was operated in negative ionisation mode. During the first half of the experiment, tuning of the source conditions was completed and the stage position location (i.e. physical location of the capillary emitter to the mass spectrometer orifice) was optimised in an attempt to produce a signal for chloramphenicol. However, only electrical discharge was observed from the emitter tip 2, observed as elevated regions within the total ion current ("TIC"), without producing an appreciable chloramphenicol signal.

The second half of the experiment was performed after a ring electrode 4 was installed. Here it can be seen that a significant chloramphenicol signal was observed without the characteristic spikes in the TIC (which are indicative of electrical discharge) demonstrating that the chloramphenicol signal is generated by genuine electrospray ionisation.

Figure 8:
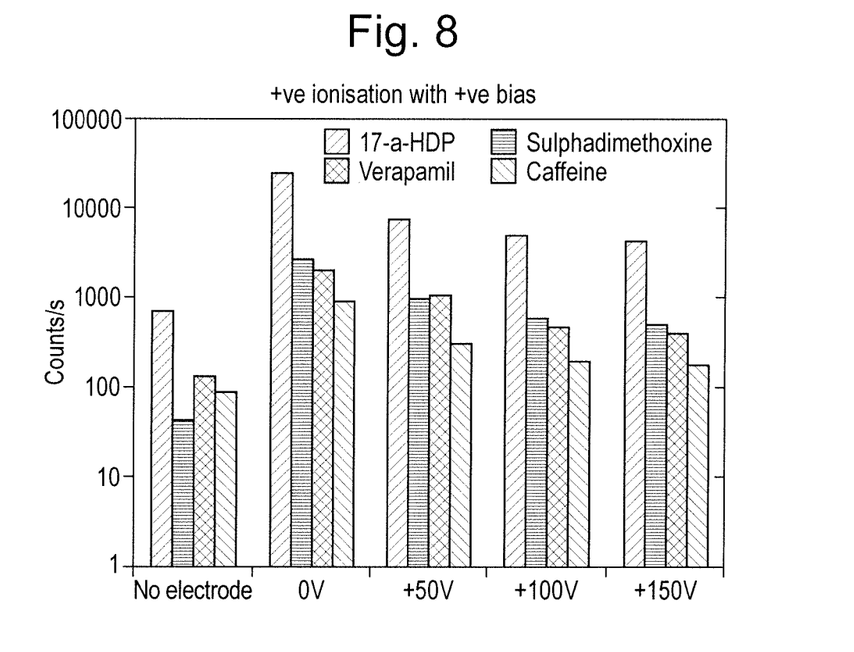
FIG. 8 shows the counts per second obtained in positive ionisation mode for four analytes in the absence of a counter electrode and with a counter electrode maintained at a bias voltage of 0V, 50V, 100V and 150V.
Figure 9:
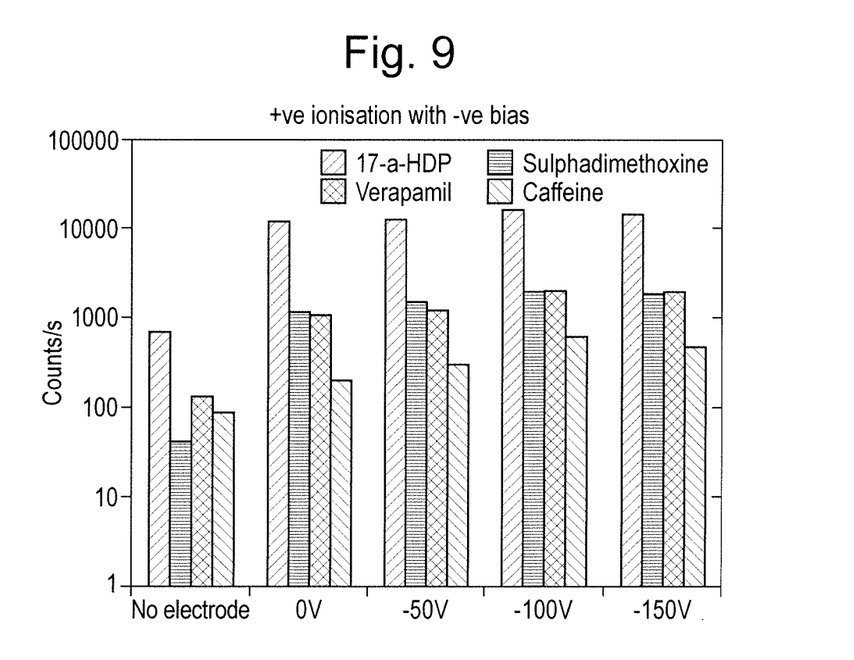
FIG. 9 shows the counts per second obtained in positive ionisation mode for four analytes in the absence of a counter electrode and with a counter electrode maintained at a bias voltage of 0V, −50V, −100V and −150V.

An improvement in response was also observed in positive ion mode. FIGS. 8 and 9 show the counts per second obtained in positive ionisation mode for four analytes (17-a-HDP, sulphadimethoxine, verapamil and caffeine). It can be seen that while all four species have a significant response without the provision of a ring electrode 4, the sensitivity is increased by approximately one order of magnitude by including a ring electrode 4 at ground (0V) according to a preferred embodiment of the present invention.

An increasing positive voltage applied to the ring electrode 4 in positive ionisation mode (FIG. 8) resulted in a decrease in the response of all four analytes while the application of a negative voltage (FIG. 9) results in a further enhancement of the observed signal.

It can be seen that on comparing the results obtained with the ring electrode 4 in position at grounded potential (0V) in FIGS. 5 and 6 that the data is slightly different when the data might be expected to be equivalent. This is also observed when comparing the data at grounded potential in FIGS. 8 and 9. This highlights a strong dependence between the magnitude of the observed benefit and the precise positioning of the ring electrode 4 relative to emitter tip 2 and the sample cone 5 or outer gas cone of a mass spectrometer. In these experiments achieving the same position reproducibly was not possible with the experimental setup available.

Further alternative embodiments are contemplated wherein the voltages applied to the electrodes may be reversed e.g. the capillary electrode 2 may be held at a ground potential (0V) and the ring electrode 4 may be held at a high (AC or DC) voltage to induce ionisation of the eluent flow.

In the case of a DC voltage, this arrangement may benefit from the use of additional field shaping electrodes to guide ions into the inlet orifice 5 of the mass spectrometer.

Embodiments are also contemplated wherein the capillary voltage may be ramped with time to provide greater control over beam stability and analyte intensity with the optimum lower capillary value.

Although the present invention has been described with reference to preferred embodiments, it will be understood by those skilled in the art that various changes in form and detail may be made without departing from the scope of the invention as set forth in the accompanying claims.

The invention claimed is:

1. An interface for a mass spectrometer comprising:
   a microfluidic substrate, tile or cartridge comprising a liquid chromatography separation column and an electrospray emitter; and
   a counter electrode arranged downstream from a tip of said electrospray emitter and arranged and adapted to direct ions towards an atmospheric pressure interface or ion inlet aperture of a mass spectrometer.

2. An interface as claimed in claim 1, wherein said counter electrode is arranged at a distance x mm downstream from said tip of said electrospray emitter, wherein: (i) x is ≤10 mm, ≤9 mm, ≤8 mm, ≤7 mm, ≤6 mm, ≤5 mm, ≤4 mm, ≤3 mm, ≤2 mm or ≤1 mm; and/or (ii) x is >0 mm, ≥0.5 mm, ≥0.6 mm, ≥0.7 mm, ≥0.8 mm, ≥0.9 mm or ≥1 mm.

3. An interface as claimed in claim 1, further comprising a voltage device arranged and adapted to apply a voltage to said electrospray emitter so as to maintain a potential difference between said electrospray emitter and said counter electrode, wherein said potential difference between said electrospray emitter and said counter electrode results in the ionisation of droplets emitted from said electrospray emitter.

4. An interface as claimed in claim 1, wherein in use a liquid sample is passed through said liquid chromatography separation column at a flow rate <250 nL/min, 250-500 nL/min, 500-750 nL/min, 750-1000 nL/min, 1-2 µL/min, 2-3 µL/min, 3-4 µL/min, 4-5 µL/min, 5-6 µL/min, 6-7 µL/min, 7-8 µL/min, 8-9 µL/min, 9-10 µL/min, 10-15 µL/min and/or 15-20 µL/min.

5. An interface as claimed in claim 1, further comprising a device arranged and adapted to introduce a nebulising flow of gas around said tip of said electrospray emitter.

6. An interface as claimed in claim 1, wherein said counter electrode comprises a ring or annular electrode or an electrode having one or more apertures.

7. An interface as claimed in claim 1, wherein said counter electrode is arranged and adapted to create a substantially uniform electric field at or in the vicinity of said electrospray emitter.

8. An interface as claimed in claim 1, wherein said microfluidic substrate, tile or cartridge is formed from a ceramic or is otherwise formed from sintered inorganic particles.

9. A mass spectrometer comprising an interface as claimed in claim 1.

10. A method of liquid chromatography comprising:
    passing a liquid through a microfluidic substrate, tile or cartridge comprising a liquid chromatography separation column and electrospray emitter;

ionising an eluent emitted from said liquid chromatography column using said electrospray emitter;

providing a counter electrode downstream from a tip of said electrospray emitter; and directing ions using said counter electrode towards an atmospheric pressure interface or ion inlet aperture of a mass spectrometer.

11. A method as claimed in claim 10, further comprising locating said counter electrode at a distance x mm downstream from said tip of said electrospray emitter, wherein: (i) x is ≤10 mm, ≤9 mm, ≤8 mm, ≤7 mm, ≤6 mm, ≤5 mm, ≤4 mm, ≤3 mm, ≤2 mm or ≤1 mm; and/or (ii) x is >0 mm, ≥0.5 mm, ≥0.6 mm, ≥0.7 mm, ≥0.8 mm, ≥0.9 mm or ≥1 mm.

12. A method as claimed in claim 10, further comprising applying a voltage to said electrospray emitter so as to maintain a potential difference between said electrospray emitter and said counter electrode, wherein said potential difference between said electrospray emitter and said counter electrode results in the ionisation of droplets emitted from said electrospray emitter.

13. A method as claimed in claim 10, further comprising passing a liquid sample through said liquid chromatography separation column at a flow rate <250 nL/min, 250-500 nL/min, 500-750 nL/min, 750-1000 nL/min, 1-2 µL/min, 2-3 µL/min, 3-4 µL/min, 4-5 µL/min, 5-6 µL/min, 6-7 µL/min, 7-8 µL/min, 8-9 µL/min, 9-10 µL/min, 10-15 µL/min and/or 15-20 µL/min.

14. A method as claimed in claim 10, further comprising introducing a nebulising flow of gas around said tip of said electrospray emitter.

15. A method as claimed in claim 10, further comprising using said counter electrode to create a substantially uniform electric field at or in the vicinity of said electrospray emitter.

\* \* \* \* \*